Dec. 22, 1942. E. PRUSHEK Plant Pat. 561
CHRYSANTHEMUM
Filed July 17, 1942
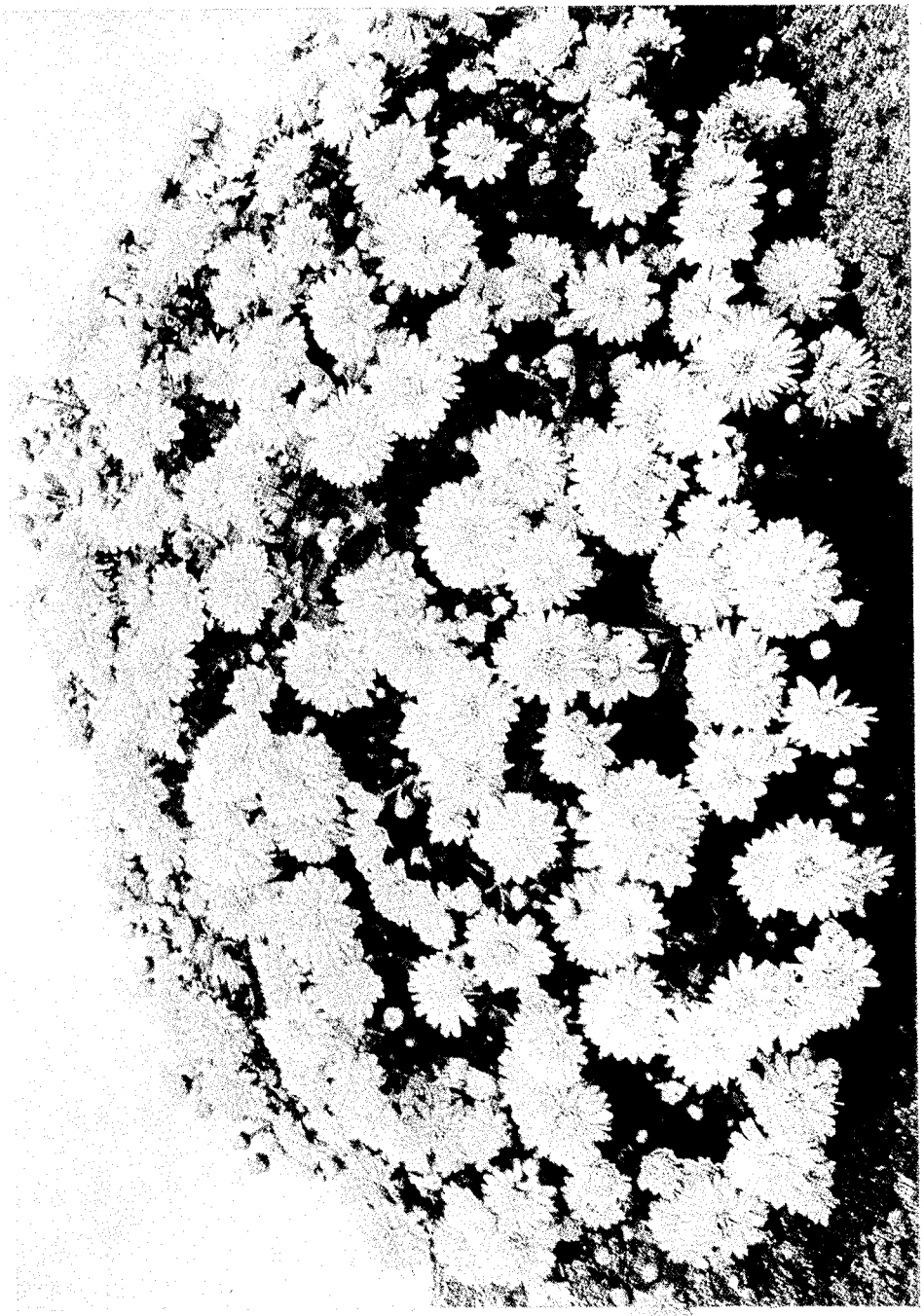
INVENTOR
Emil Prushek
BY Robb & Robb
ATTORNEYS Patented Dec. 22, 1942

UNITED STATES PATENT OFFICE

561

CHRYSANTHEMUM

Emil Prushek, Benton Harbor, Mich., assignor to The R. M. Kellogg Company, Three Rivers, Mich.

Application July 17, 1942, Serial No. 451,326

1 Claim. (Cl. 47—60)

My present invention consists of a new and distinct variety of chrysanthemum, and comprises a plant of this type having desirable qualities in reference to thrifty growth, but which is particularly unique by reason of the color variations of the individual flowers of the plant in full bloom and over its blooming period. The color variations create unusual effects of opalescence, making the plant particularly attractive. Also, the plant maintains its attractiveness of blooming when it fades, as distinguished from the types of chrysanthemums which, in fading, are almost white, or colorless.

My above described plant is also characterized by its long blooming period, running from approximately the middle of August until the coming of heavy frost in the fall.

The plant lives through the northern winters of this country with only an ordinary amount of winter protection.

My said plant has been obtained by crossing the variety White Cushion with Amelia, and, generally describing the chrysanthemum of this invention, it is noted that the same has the following primary characteristics:

(*a*) The plant is very vigorous and grows to a well rounded cushion shape, attaining an average diameter of 20″ in reasonably fertile soil, and a larger size in more rich soil. The height of the plant will average about 10″.

(*b*) In its habit of growth my new variety of chrysanthemum is similar to Amelia except that it grows lower and is more compact.

(*c*) The foliage of the plant is a healthy and attractive green and is apparently resistant to chrysanthemum leaf spot, showing no damage from this disease, while Sandra and Ann Miller plants in adjacent beds were completely defoliated by said disease.

(*d*) My plant reproduces itself well by sending out many strong sprouts around its base.

(*e*) Respecting hardihood, not a single plant was lost by winter injury during the winter of 1941–42 and where the plants were grown at Hartford, Michigan, with no protection of any kind and located in different fields and on different types of soil.

In addition to the foregoing, and reverting to the main distinguishing feature of my plant, this consists of the unusual or unique color variations of the flowers of the plant when in full bloom. The early buds open to Pinard Yellow just as the sepals begin to divide, and change to Orange Buff as the petals unfurl. As the flower approaches full bloom the color changes to Geranium Pink at the tips of the petals and approaches Grenadine near the center, while the tips and reverse of the center petals show Amber Yellow. As the flower reaches full bloom the tips of the petals retain the Geranium Pink color which blends into Rose Doree toward the center of the flower and then to a mixture of Grenadine and the Amber Yellow of the tips and reverse of the petals in the center of the flower. From this stage the flowers gradually change to a predominant color of Capucine Buff with center petals showing Lemon Yellow. As the flower fades with age, it takes on a predominant color of Light Phlox purple that remains until flowers are destroyed by cold weather.

The above description of the flower colors is based on colors selected from Ridgway's Color Standards.

In other words, the coloring of the plant is not confined to any single color but varies during its blooming period with the coloring characteristics above described. Even in the fading period of the blooms the attractiveness of the coloring variation continues to be present, as distinguished from Amelia which opens up to show yellow centers and fades to almost white during such period.

The following is a detail description of this new variety of chrysanthemum and the color terminology employed in the following is in accord with Ridgway's Color Standards where indicated by plate numbers, or in accord with the Horticultural Color Chart issued by the British Color Council, as indicated.

Type: Seedling.

Breeding: Seedling.

Seed Parent.—"White Cushion."

Pollen Parent.—"Amelia."

Classification:

*Botanical.*—"Chrysanthemum Hortorum."

Propagation: Holds its distinguishing characteristics through succeeding propagations by cuttings, grafting, and budding.

*Flower*

Locality where grown: Hartford, Michigan.

Bud:

*Peduncle.*—Short and nested in foliage; slightly pubescent; medium green in color; in strength stiff, erect, and slender.

*Form.*—Medium size and globular; is not affected by hot weather or wet weather.

*Color.*—When sepals first divide—(Ridgway) Pinard Yellow, Plate 4, 21, 0–YY*d*. (Horticultural) Canary Yellow 2/2. When petals begin to unfurl—(Ridgway) Orange Buff, Plate 15, Y–0*d*. (Horticultural) Apricot 609/1. *Midseason and late buds*—when half blown—(Ridgway) Bittersweet Pink, Plate 2, 9, OR–*o*. (Horticultural) Saturn Red 12/2.

*Opening.*—Opens up well and is not affected by adverse conditions.

*Bloom*

Size: Medium.
Borne: Several together.
Stems: Short; normal strength.
Petalage: Average 10 rows of petals; very double (many petals and stamens hidden); about 135 petals under normal conditions.
Color of flower:
*Early flowers.*—Full bloom flower—predominating color—(Ridgway) Geranium Pink, Plate 1, 3, 0–R,*d*. (Horticultural) Azalea Pink 618/1. Center color—(Ridgway) Grenadine, Plate 2, 7, R–0,*b*. (Horticultural) 614/1 Chinese Coral. Tip edge and reverse of center petals—(Ridgway) Amber Yellow, Plate 21, 21, 0–*yy*,*b*. (Horticultural) Aureolin 3/2. Reverse of petals—(Ridgway) Shell Pink, Plate 28, 11″, Orange *f*. (Horticultural) Azalea Pink 618/3. Graduating to—(Ridgway) Geranium Pink, Plate 1, 3, 0–R,*d*. (Horticultural) Azalea Pink 618—at edges of petals.
*Mid-season flowers.*—Full blown flowers—predominating color at tip of petals—(Ridgway) Geranium Pink, Plate 1, 3, 0–R,*d*. (Horticultural) Azalea Pink 618/1. Graduating to—(Ridgway) Rose Doree, Plate 1, 3, 0–R,*b*. (Horticultural) Carmine Rose 621. Centers—(Ridgway) Grenadine, Plate 2, 7, R–0,*b*. (Horticultural) Chinese Coral 614/1. Petals tipped and reversed with—(Ridgway) Amber Yellow, Plate 16, 21, 0–YY,*b*. (Horticultural) Aureolin 3/2.
*Late or faded flowers.*—Predominant color—(Ridgway) Capucine Buff, Plate 3, 13, OY–0,*f*. (Horticultural) Apricot 609/3. Center petals—(Ridgway) Lemon Yellow, Plate 4, 23, Yellow. (Horticultural) Aureolin 3/1. Final predominant color—(Ridgway) Light Phlox purple, Plate 11, 65, RR–V,*d*. (Horticultural) Mallow Purple, 630/2.

The foregoing color data has been made from past records based primarily upon Kodachrome transparencies and blossoms of small pot plants which do not bloom in their normal color at the season of the year when this application is made. The said data was made in reference to blooming flowers that matured in mid-August and afterwards in 1941, the first blossoms opening up about August 23d of that year.

Petals:
*Petaloids in center.*—None.
*Persistence.*—Hang on.
*Lastingness.*—Very long.

Genital organs:
*Stamens, anthers.*—Few.
*Stamens, filaments (threads).*—Medium to short. *Color:* Lemon Yellow.
*Pollen.*—Gold yellow.
*Styles.*—Single; medium.
*Ovaries.*—All enclosed in calyx.
Fruit: Sterile.

*Plant*

Form: Cushion type bush.
Growth: Vigorous; dwarf; branching; compact.

*Foliage*

Size: Medium.
Quantity: Abundant.
Color: *New foliage.*—Upper side—normal green (Ridgway, Plate 6, Grass Green); under side—(Ridgway, Plate 17, Light Bice Green).
*Old foliage.*—Upper side—dark green (Ridgway, Plate 6, Cedar Green); under side—(Ridgway, Plate 17, Light Elm Green).
Shape: Ternate.
Texture: Leathery; smooth.
*Under side.*—Velvety; very slight pubescence.
*Ribs and veins.*—Ordinary.
Edge: Serrated; sinuate.
Serration: Single, deep.
Leaf stem: green in color; under side slightly pubescent.
Stipules: None.
Disease resistance: Resistant to chrysanthemum leaf spot.

*Wood*

New wood:
*Color.*—Light green.
*Bark.*—Smooth.
Old wood:
*Color.*—Reddish brown.
*Bark.*—Smooth.

*Further description.*—The full flowers of this new variety of chrysanthemum open about mid-August or August 20th of the year. The early flowers are generally lighter tints than those that appear later in the season. For this reason I have designated three sets of colors from the color charts to indicate the colors of the flowers at these various stages: early flower; mid-season flower; and late or faded flowers.

I claim:

A new and distinct variety of chrysanthemum characterized as to novelty by its thrifty and vigorous growth and the unusual and unique variation in the colors of the blooms throughout its blooming period, creating the effect of opalescence substantially as shown and described.

EMIL PRUSHEK.